United States Patent [19]
Stafford et al.

[11] Patent Number: 5,473,256
[45] Date of Patent: Dec. 5, 1995

[54] COMBINATION MICROWAVE WAVEGUIDE AND PRESSURE BARRIER

[75] Inventors: Joseph D. Stafford, Bellaire; Gregory J. Hatton, Kingwood; David A. Helms, Houston, all of Tex.

[73] Assignee: Texaco Inc., White Plains, N.Y.

[21] Appl. No.: 301,937

[22] Filed: Sep. 7, 1994

[51] Int. Cl.⁶ .............................. G01R 27/04; H01P 3/16
[52] U.S. Cl. .............................. 324/636; 324/84; 324/94; 324/632; 333/239
[58] Field of Search .................................. 324/632, 636, 324/637, 639, 640, 95, 84; 73/40.5 A, 592, 644, 861.27, 861.28; 333/239, 242, 248

[56] References Cited

U.S. PATENT DOCUMENTS

| | | | |
|---|---|---|---|
| 4,149,423 | 4/1979 | Zuckerwar et al. | 73/647 X |
| 4,270,083 | 5/1981 | Fitzky et al. | 324/636 |
| 4,374,477 | 2/1983 | Kikuchi et al. | 73/861.27 |
| 4,463,330 | 7/1984 | Yoneyama | 333/239 |
| 4,651,085 | 3/1987 | Sakurai et al. | 324/636 |
| 5,369,368 | 11/1994 | Kassen et al. | 324/636 X |

*Primary Examiner*—Kenneth A. Wieder
*Assistant Examiner*—Diep Do
*Attorney, Agent, or Firm*—James L. Bailey; Kenneth R. Priem; William J. Beard

[57] ABSTRACT

A waveguide and pressure barrier for use with devices for measuring fluid parameters of fluids passing in a pipe under high temperature and pressure conditions and utilizing microwave energy for making the measurements, the device including a pair of substantially identical members adapted to be mounted in spaced opposition on the pipe. Each member has an axial bore with a transverse bore for receiving a microwave antenna. The axial bore is substantially filled with a ceramic glass material providing the pressure and temperature barrier.

5 Claims, 2 Drawing Sheets

COMBINATION MICROWAVE WAVEGUIDE AND PRESSURE BARRIER

BACKGROUND OF THE INVENTION

1. Field of the Invention

The present invention relates to a waveguide and pressure barrier and in particular to one using a glass ceramic material sealed into a compatible metal member for use in high pressure, high temperature fluid measurement devices.

2. The Prior Art

Heretofore waveguide/pressure barriers have been made from TEFLON® or other materials that are subject to changes in shape due to both temperature and pressure variations. These changes in shape degrade the performance and limit the range of use of associated instruments such as water cut and three phase fluid monitors.

SUMMARY OF THE INVENTION

The present invention concerns a waveguide and pressure barrier which uses a glass/ceramic material sealed into a compatible metal member so as to enable fluid measurements over wide ranges of temperature and pressures without adverse affect.

BRIEF DESCRIPTION OF THE DRAWINGS

The present invention will now be described, by way of example, with reference to the accompanying drawings in which.

DETAILED DESCRIPTION OF THE PREFERRED EMBODIMENT

The present invention 10 is shown in connection with a pipe 12 which carries oil/water/gas or other multi-phase fluids under high temperature and pressure. The subject invention is used in conjunction with a device measuring one or more parameters of a fluid, such as water cut monitor or multi-phase monitoring device (neither of which has been shown).

Figure 1:
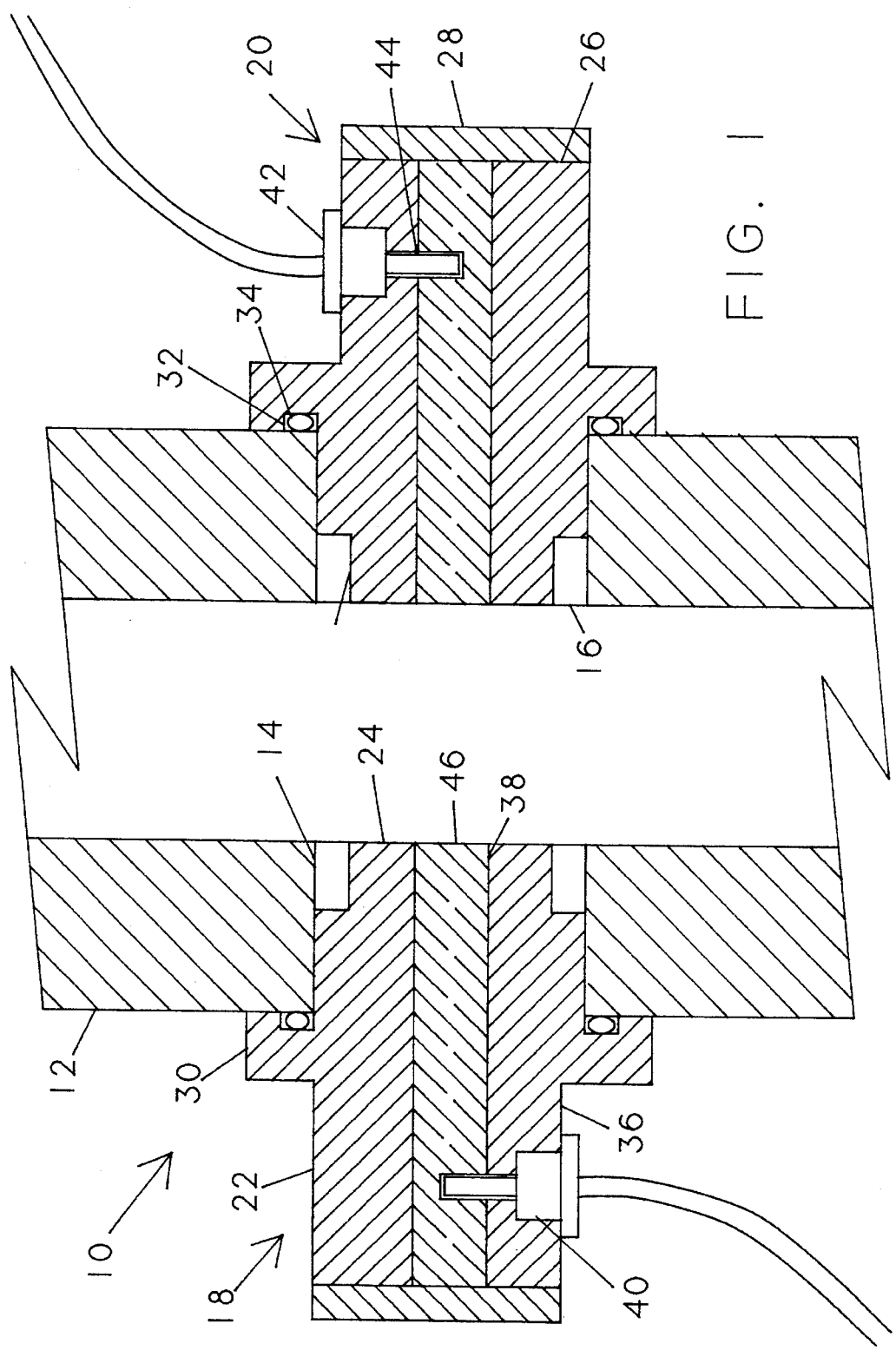
FIG. 1 is a longitudinal section taken along line 1—1 of FIG. 3 showing the present invention installed in a pipe of a fluid measurement device.
Figure 2:
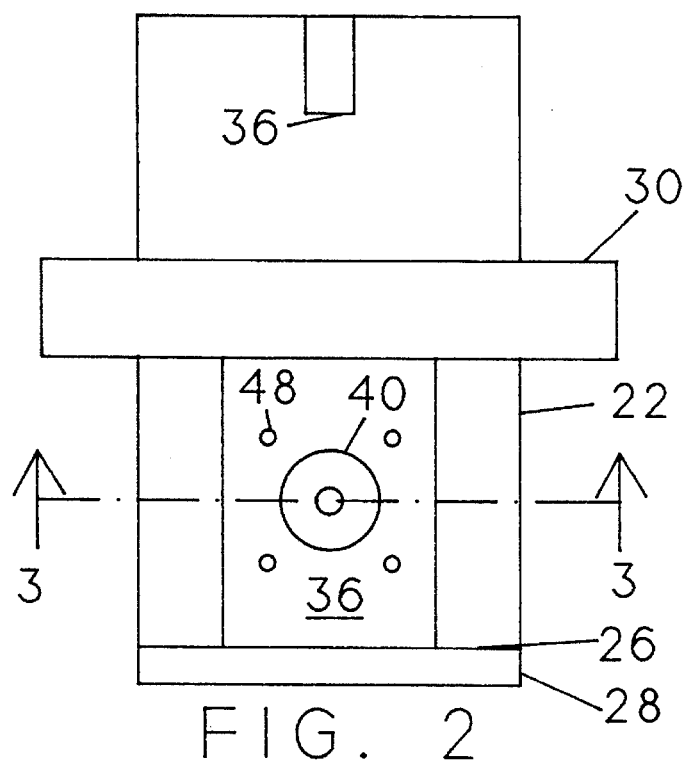
FIG. 2 is a top plan view an insert member of the present invention.
Figure 3:
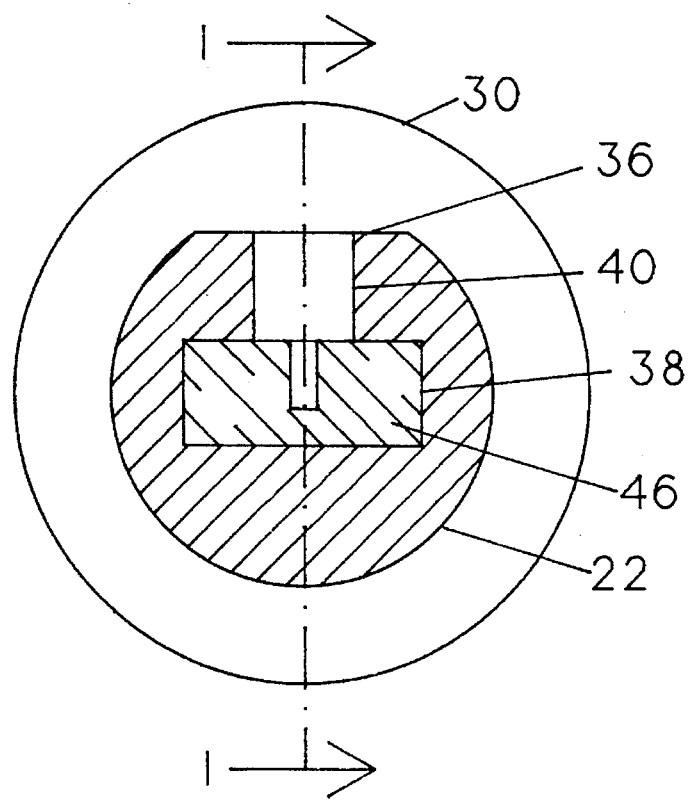
FIG. 3 is a transverse section taken along line 3—3 of FIG. 2.

The pipe 12 is provided with a transverse bore 14 across a diameter thereof. The bore preferably includes keying means 16 such as an alignment pin as shown. The present invention is formed by like metal insert members 18, 20, each of which is a metal member with a generally cylindrical outer profile 22 adapted to be received in bore 14 and extending between a front face 24 and a rear face 26, which is covered by plate 28. A flange 30 extends radially outwardly intermediate the ends with an annular groove 32 directed toward face 24 and receiving therein annular sealing ring 34. At least one keying means, such as notch 16, is formed in the front face 24 for engaging keying means 16A to align members 18,20 on opposite sides of pipe 12. A portion of the outer surface between rear face 26 and flange 30 is machined flat to form surface 36. An axial bore 38, preferably in the shape of a rectangular cross sectioned microwave waveguide, extends between faces 24 and 26. A profiled transverse bore 40 in surface 36 intercepts the axial bore 38 near the rear end thereof. The transverse bore 40 is adapted to receive a coaxial cable plug 42, which is connected to a microwave source or receiver, respectively, (not shown). The antenna 44 of the plug extends into the axial waveguide bore 38 coupling the microwave signal thereto. The axial bore 38 is substantially filled by a glass-ceramic material 46, preferably of a type known as S-Glass. Surface 36 (FIGS. 2 and 3 is shown with a plurality of threaded bores 48 which may be used for mounting the plugs 42 in the members 18, 20.

Preferably the glass-ceramic material 46 is melted into the axial bore 38 and both the member 18, 20 and the included material are carefully held at several temperatures during ramp up and ramp down of an oven. This forms a good seal between the glass-ceramic material 46 and the metal surface of the members 20, 18 thereby preventing the leakage of pressure and providing a consistent microwave boundary. The front face 24 of each member is then machined to form a flat surface across the metal and glass.

The keying means assure proper orientation of members 20, 18 so that the waveguides thereof are aligned. Known retaining means (not shown) are used to secure the members 20, 18 against the pipe 12 in conventional fashion.

The preferred material for filling the axial bores is a glass ceramic material supplied by Ceramaseal of New Lebanon, N.Y. This material is permeable to microwave signals but strong enough to be used under extreme temperatures common in the chemical industry. It is an ideal replacement for the current TEFLON® or glass type windows which have high failure rates under high temperature conditions. This material will suitably function over a wide range of temperatures ranging from cryogenic to 450° C. and will even function in the high vacuum environment of space. The preferred material for the insert members is steel.

The present invention may be subject to many modifications and changes without departing from the spirit or essential characteristics thereof. The present embodiment should therefore be considered in all respects as illustrative and not restrictive of the scope of the invention as defined by the appended claims.

We claim:

1. A combination waveguide and pressure barrier for use with equipment for making a microwave measurement of fluids flowing in a pipe under high temperature and high pressure conditions comprising:

a pair of like metal members of generally cylindrical configurations having a first closed end and a second opposite open end and adapted to be mounted in spaced diametrical opposition from each other on the pipe carrying the fluid to be measured;

an axial bore through each of said members closed at one end thereof and forming a microwave frequency waveguide;

a transverse-bore intercepting each said axial bore near the opposite open end from said first closed end thereof;

coaxial cable connector means each adapted to be received in a respective one of said transverse bores and terminating with an antenna extending into said axial bore for coupling microwave frequency energy to said axial bore; and a glass ceramic material substantially filling said axial bore and forming a fluid tight high temperature and pressure seal with said member.

2. The member according to claim 1 further comprising circumferential flange means extending radially from the outer surface of said generally cylindrical members and including sealing means on a face of said flange means and adapted to be mounted in sealing engagement with said pipe.

3. The member according to claim 1 wherein said axial bore has a transverse section sized so as to be conducive to transmission of microwaves energy.

4. The member according to claim 3 wherein said transverse section is rectangular.

5. The member according to claim 1 further comprising keying means for assuring axial alignment and orientation of said pair of like metal members when mounted on said pipe.

\* \* \* \* \*